(12) United States Patent
Deodhar et al.

(10) Patent No.: US 11,612,406 B2
(45) Date of Patent: *Mar. 28, 2023

(54) COMBINATIONAL SCISSOR-GRASPER TOOL FOR USE IN LAPAROSCOPY

(71) Applicant: Intuitive Surgical Operations, Inc., Sunnyvale, CA (US)

(72) Inventors: Chinmay Deodhar, Kothrud (IN); Asokan Thondiyath, ITT Madras (IN)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 327 days.

This patent is subject to a terminal disclaimer.

(21) Appl. No.: 16/811,859

(22) Filed: Mar. 6, 2020

(65) Prior Publication Data

US 2020/0205847 A1 Jul. 2, 2020

Related U.S. Application Data

(63) Continuation of application No. 14/499,418, filed on Sep. 29, 2014, now Pat. No. 10,617,439, which is a continuation of application No. 13/503,773, filed as application No. PCT/IB2011/052723 on Jun. 22, 2011, now Pat. No. 8,870,902.

(30) Foreign Application Priority Data

Jun. 23, 2010 (IN) .......................... 1852/MUM/2010

(51) Int. Cl.
| | |
|---|---|
| *A61B 17/295* | (2006.01) |
| *A61B 17/3201* | (2006.01) |
| *A61B 17/00* | (2006.01) |
| *A61B 17/29* | (2006.01) |

(52) U.S. Cl.
CPC ........ *A61B 17/295* (2013.01); *A61B 17/3201* (2013.01); *A61B 2017/00353* (2013.01); *A61B 2017/2926* (2013.01); *A61B 2017/2938* (2013.01)

(58) Field of Classification Search
CPC .............. A61B 17/295; A61B 17/3201; A61B 2017/00353; A61B 2017/2926; A61B 2017/2938
See application file for complete search history.

(56) References Cited

U.S. PATENT DOCUMENTS

| | | |
|---|---|---|
| 5,336,228 A | 8/1994 | Cholhan |
| 5,509,923 A | 4/1996 | Middleman et al. |
| 5,542,949 A | 8/1996 | Yoon |

(Continued)

FOREIGN PATENT DOCUMENTS

EP 2368504 A1 9/2011

OTHER PUBLICATIONS

Extended European Search Report for Application No. 11797712.4, dated Jun. 21, 2017, 9 pages.

(Continued)

*Primary Examiner* — Brooke Labranche

(57) ABSTRACT

Disclosed is a four-jawed combinational scissor-grasper surgical tool for use in laparoscopy. Cutting and grasping functionalities are respectively enabled via movement of a pair of such specially contoured jaw members sliding against or splaying apart from the other pair. Also disclosed are means for achieving selectable interlocking of jaw members and mechanical linkage for their actuation by human user.

14 Claims, 11 Drawing Sheets

(56) References Cited

U.S. PATENT DOCUMENTS

| | | | |
|---|---|---|---|
| 5,637,111 | A | 6/1997 | Sutou et al. |
| 5,919,206 | A | 7/1999 | Gengler et al. |
| 6,024,744 | A | 2/2000 | Kese et al. |
| 6,030,384 | A | 2/2000 | Nezhat |
| 6,520,960 | B2 | 2/2003 | Blocher et al. |
| 8,870,902 | B2 | 10/2014 | Deodhar et al. |
| 10,617,439 | B2 | 4/2020 | Deodhar et al. |
| 2003/0055424 | A1 | 3/2003 | Ciarrocca |
| 2005/0072827 | A1 | 4/2005 | Mollenauer |
| 2007/0179525 | A1 | 8/2007 | Frecker et al. |
| 2010/0057085 | A1 | 3/2010 | Holcomb et al. |
| 2010/0122419 | A1 | 5/2010 | Zupancic-Albin |
| 2011/0238066 | A1 | 9/2011 | Olson et al. |
| 2012/0029305 | A1 | 2/2012 | La et al. |

OTHER PUBLICATIONS

Extended European Search Report for Application No. 18211650.9, dated Sep. 12, 2019, 7 pages.
International Search Report and Written Opinion for Application No. PCT/IB2011/52723, dated Nov. 23, 2011, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

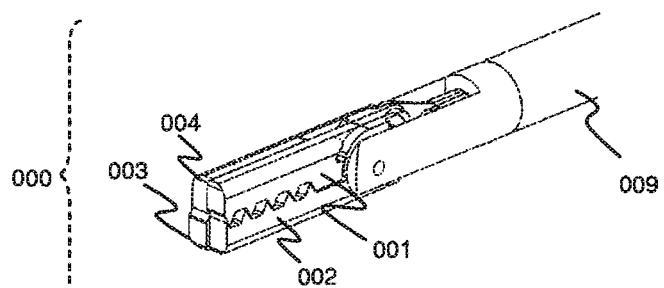
Fig. 4.a
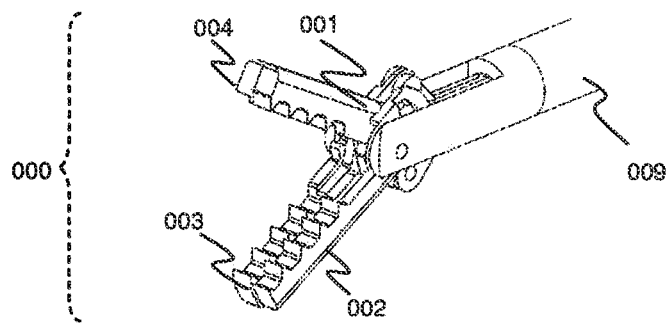
Fig. 4.b
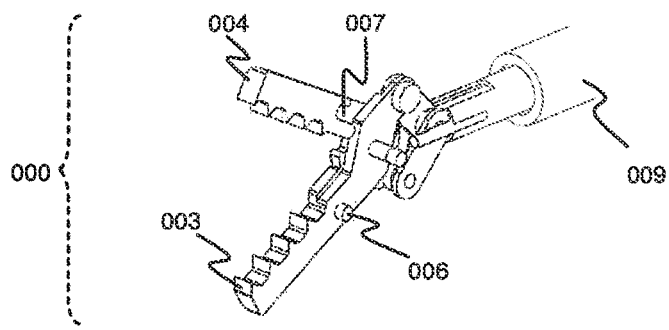
Fig. 4.c

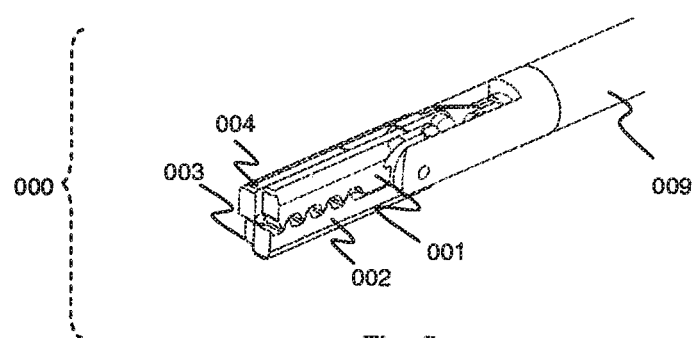
Fig. 5.a
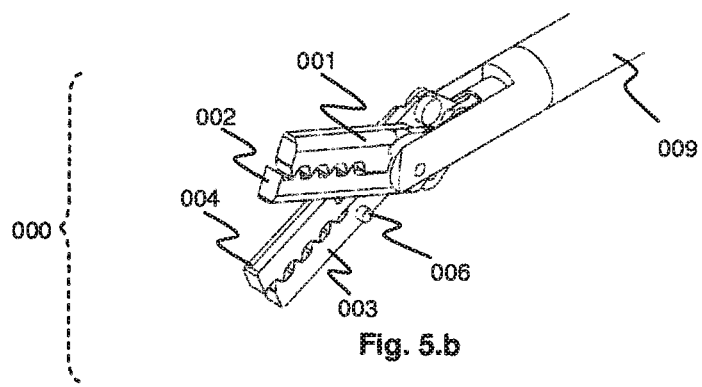
Fig. 5.b
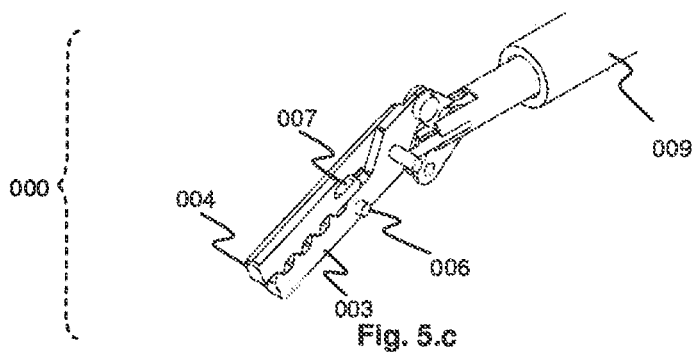
Fig. 5.c

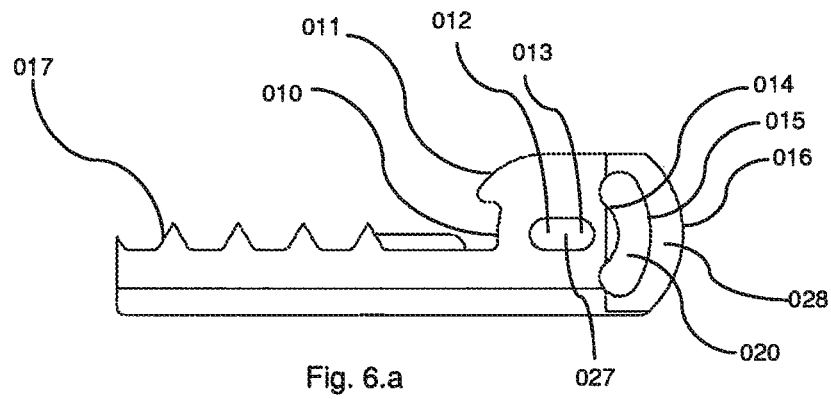
Fig. 6.a
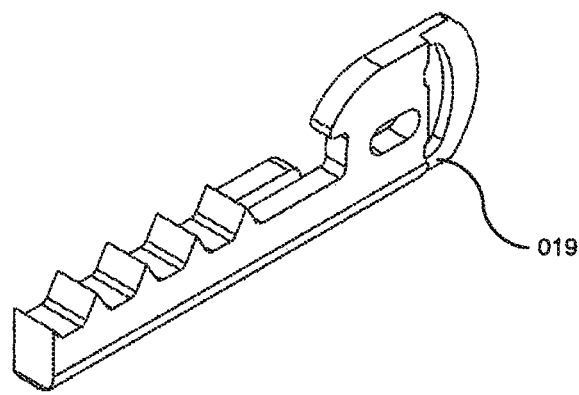
Fig. 6.b
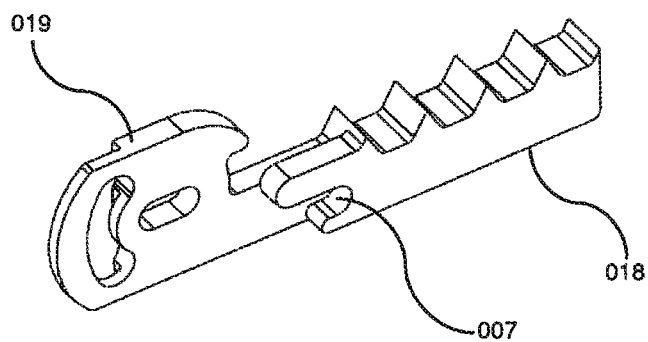
Fig. 6.c

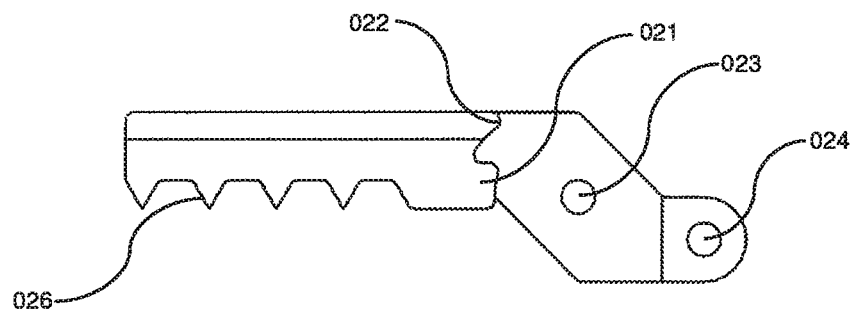
Fig. 7.a
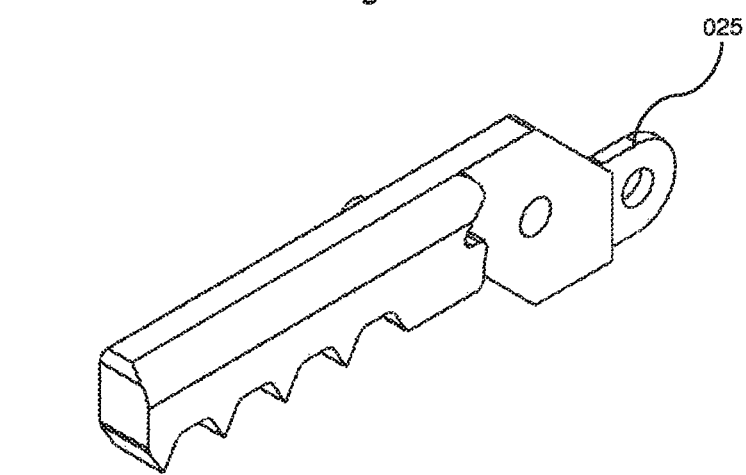
Fig. 7.b
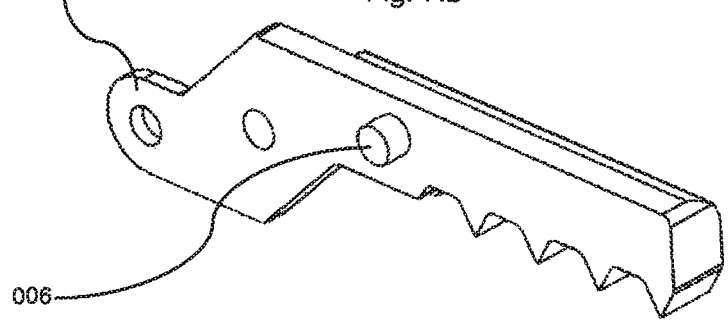
Fig. 7.c

COMBINATIONAL SCISSOR-GRASPER TOOL FOR USE IN LAPAROSCOPY

FIELD OF THE INVENTION

The present invention generally relates to art of surgical tools and more specifically to the architecture and operation of a bi-functional scissor-grasper tool capable of being used in minimally invasive surgical procedures such as laparoscopy.

BACKGROUND OF THE INVENTION

Past few decades have seen vast development as to surgical procedures—minimally invasive surgery being one of the prime advances of this era. Minimally invasive surgeries, such as arthroscopic surgery and laparoscopic surgery, recently have become widely practiced surgical procedures. Such procedures have gained rapid popularity and generally are preferable over the traditional open surgery which requires cutting large incisions through the skin, muscles and membranes to open and expose the body cavity, thereby necessitating longer hospitalization stays and prolonged recovery periods. In minimally invasive surgery, small incisions are made into which tubular conduits, such as cannulae and trocars, are inserted and directed to the site of the operable internal organ or tissue. One or more surgical instruments are introduced, each through individual tubular conduits in order to perform the surgical procedure. It would be obvious to the reader that said minimally invasive surgical procedures including arthroscopy, endoscopy and laparoscopy owe their realization to special tools capable of access to intended site of surgery via small incision made to body of patient and operation of which allows precise performance of intended site-specific surgical manipulations.

Cutting, grasping, suturing, cauterization, distension, stapling form commonality of operations in surgery. Minimally invasive surgery tools of art do provide individually for such functions. However, due to the singularity of function accorded by such tools available, the interchange of tools amidst operations and efforts, time required for such becomes unavoidable, besides causing opportunity for complications during repeated insertion and removal of different tools.

In laparoscopic surgery, specialized long thin tools are inserted via air-tight ports fixed on the $CO_2$ inflated abdomen of the patient. The operation area as seen by the endoscope is displayed on an external display where the surgeon views it.

Since only a few thin holes are created for inserting tools, this type of surgery results in fewer injuries to the patient, faster healing periods and less cosmetic damage. This type of surgery requires specialized tools that are characterized by their long shafts (usually around 300 mm) and thin cross sections (usually 5-8 mm dia). These tools come in various end-tips, such as scissors, blades, graspers, etc. Procurement/maintenance costs, sterilization requirements of additional equipment are other problems faced by the medical fraternity. Thus, development of minimum invasive surgical tools capable of plural functionality, yet maintaining accuracy, precision and ease of use, are pressing needs of art.

There have been some attempts for resolving said needs of art. Various forms of laparoscopy tools, housings for positioning instruments, extendible blades, multifunctional scissor jaw designs and the like find mention in the art. Many devices which are used commonly for grasping or cutting objects have two elements which can be moved towards one another and away from one another. The elements have surfaces which may be blunt or sharp so that an object positioned between them may be either grasped or cut when the elements are moved towards one another. Examples of such devices include tongs, tweezers, forceps, scissors, guillotines, and wire cutters. Such devices can also be adapted to dissect tissue, for example, by placing the elements of the device into or next to an object and then causing the elements to splay apart thereby dissecting the object. However, these designs have been found to suffer from drawbacks critically affecting their intended function.

U.S. Pat. No. 6,024,744 discloses a combined bipolar scissor and grasper. The instrument disclosed in this patent is a combined bipolar electrosurgical cutting and grasping instrument where the grasping surfaces are contained within the shape of a standard surgical scissor. Accuracy of operation is defined by precise positioning of these portions at site of manipulation. However, being contained within same arm, the cutting and grasping portions are invariably in same angle of motion, thus present risk of accidental cuts or clamps. Also, pivoting of the tool while being inserted is not without risk due to exposed cutting edges.

U.S. Pat. No. 5,397,325 discloses a surgical suturing device which has a tubular elongated shaft terminating into a jaw assembly at the distal end and a handle assembly at the proximal end thereof. The jaw assembly includes a first jaw member pivotally connected to a second jaw member. An actuator rod extending longitudinally within the length of said shaft is connected at its proximal end to said handle assembly and is pivotally connected at its distal end to said jaw assembly. The underside of said first jaw member is provided with a cupped recess having a wheel assembly disposed therein. The wheel assembly includes a needle mount for securely retaining a needle and is configured such that the needle lies within the cupped recess when the jaw members are closed and can be deployed in a protracted position away from the first jaw member when the jaw members are in an open position. In operation, the suturing device offers superior control over both the needle and the tissue to be sutured.

The above mentioned invention suffers from drawback of limited degree of operation due to configuration wherein only one jaw is movable and the other fixed. The said single shaft device presented finds utility for function of suturing having adequate needle control, however, does not offer means to grasp and stabilize the tissue, which is slippery by nature thus mandating that the tissue tending to evade needle carrier manipulation must be grasped by a second instrument. As a result, the surgeon encounters difficulty in controlling and positioning both the needle and the tissue simultaneously, and the patient can suffer complications such as frayed tissue, errant punctures, inadequate stitches, extended surgical duration, hemorrhaging, and the like.

U.S. Pat. No. 5,509,923 describes a device for dissecting, grasping and/or cutting an object has at least two elongate elements at least a portion of at least one of the elements is formed from a pseudoelastic material, preferably a pseudoelastic shape memory alloy. End portions of the elements can be moved away from one another and then toward one another to dissect, grasp and/or cut an object with the elements. In certain embodiments, the device further comprises an actuating means and at least a portion of the elements and/or the actuating means is formed from a pseudoelastic material. The device is intended for applications including dissecting, grasping and/or cutting objects located in difficult to reach areas, within the body during surgery. However, the cutting/grasping members of this tool are pseudoelastic and thus, allow limited degree of choice while deciding on the angle of cut and portion of tissue being grasped. Unintentional nicks and pinches cannot be ruled out are limitations in rotational ability of the tool proposed.

Laparoscopic Scissor Grasper, a product by Interventional and Surgical innovations LLC is a minimally invasive surgery tool that can both cut and grasp with aid of two jaws having mated via serrations along their inner surfaces. The jaws separate along two axes apart and sideways to provide grasping and cutting functions respectively. However, this design is subject to certain shortcomings as the grasping serrations are invariably exposed while shearing. Also, pivoting of the jaws about their longitudinal axis is not possible. Also, for cutting edge to work, the chamfered edges necessarily need to press against each other. This pressure is enabled by forging a slight curvature in cutting arms being pressed at pivot by means of rivet or other tightening means. Over period of use, this arrangement looses its original construction leading to either loss of pressure of cutting arms or distancing of said cutting arms which ultimately leads to firstly loss of cutting functionality and secondly, presence of two sharpened (chamfered) edges which act as knives and can cut whether intended or not. Such occurrence, is thus compromise to application intended.

U.S. Pat. No. 5,133,727 discloses radial jaw biopsy forceps which feature a multi element head having a fixed blade juxtaposed between two grasper jaws having mated serrations along their internal edges for grip. However, this design too has shortcomings of limited scope for movement and accidental cuts to material in space between the grasping arms while performing delicate functions.

By and large, innovations cited have not been able to overcome the problems of the art. Design of a pluri-functional device for achievement of surgical operations is a pressing need of the art. The present inventor has undertaken specific research and has arrived at novel construction and operability of a device for addressing said problems of art. The following brief description presents one non-limiting embodiment of constructing and performing the present invention.

OBJECTS OF THE PRESENT INVENTION

It is an object of the present invention to provide a single shaft four-jawed laparoscopic instrument with suitable components and linkages that provide for cutting-grasping bi-functionality and construction capable of performing intended bi-functionality in a manner that allows infinite rotational ability about its longitudinal axis.

It is another object of the present invention to provide a single shaft laparoscopic instrument wherein cutting functionality is enabled via shear forces achieved at edges of jaws by their motion against each other thus avoiding open blade design altogether.

It is another object of the present invention to provide a four-jawed single shaft laparoscopic instrument wherein construction of jaws comprise integral mechanical interlocking system that allows for selectable locking of two pairs of jaws each configuration serving the cutting or grasping functionalities.

It is another object of the present invention to provide a bi-functional single shaft laparoscopic instrument which reduces the amount of instrumentation necessary for surgical procedures in which both cutting and grasping is required.

It is another object of the present invention to provide a bi-functional single shaft laparoscopic instrument which reduces the amount of dexterity needed by a surgeon performing a surgical procedure in which both electrosurgical cutting and grasping is required.

It is another object of the present invention to provide a bi-functional single shaft laparoscopic instrument which is easily amenable to common art pre-surgical sterilization techniques.

It is another object of the present invention to provide a bi-functional single shaft laparoscopic instrument which is capable of repeated use thus decreasing the amount of medical waste generated in surgical procedures.

It is yet another object of the present invention to provide for a minimally invasive surgical tool which efficiently combines functions of cutting, grasping and overcomes overall drawbacks of prior art devices.

It is also an object of the present invention to achieve accurate fine cuts or shear-free firm grasp whenever intended.

It is also an object of the present invention to provide grasping and cutting surfaces which are independent of each other.

These and further objects shall present themselves to the reader upon description presented herein below along with accompanying drawings.

SUMMARY OF THE PRESENT INVENTION

In accordance with principles of the present invention, a single shaft laparoscopic instrument is proposed which has cutting/grasping bi-functionality. Said bi-functionality is enabled by achieving two user-selectable configurations of four specially constructed jaw members. Design of these jaw members comprises an integral mechanical interlocking system and linkage which, when operated by the user, results in two movable elements each comprising a pair of jaws. In one configuration where linkage allows for sliding of the movable elements against each other, cutting function is achieved. In other configuration where linkage allows for movement of the movable elements away from and towards each other, the grasping functionality is achieved.

The invention may be more fully understood by reference to the cited figures and details of exemplary embodiments. Alternative embodiments of the invention as claimed, and providing the benefits of the novel concepts of the invention, are contemplated and will be obvious from the explanations hereinafter.

BRIEF DESCRIPTION OF THE DRAWINGS

FIG. 4 (a,b,c) are schematic representation of inter-play between two jaw pairs when in grasping configuration.

FIG. 5 (a,b,c) are schematic representation of inter-play between two jaw pairs when in cutting configuration.

FIG. 6 (a,b,c) are side, front perspective and back perspective views of jaw element 002/004 of the laparoscopic instrument proposed by the present invention.

FIG. 7 (a,b,c) are side, front perspective and back perspective views of identical jaw element 001/003 of the laparoscopic instrument proposed by the present invention.

The invention may be more fully understood by reference to the cited figures and details of exemplary embodiments. Alternative embodiments of the invention as claimed, and providing the benefits of the novel concepts of the invention, are contemplated and will be obvious from the explanations hereinafter.

DETAILED DESCRIPTION OF THE INVENTION

The laparoscopic procedure generally involves creating small incisions through the navel and through the abdominal wall for viewing and operating on internal areas of the body, such as the uterus, ovaries, gall bladder and appendix. Typically, a trocar tube is introduced through the navel incision for receiving a camera, magnifying lens or other fiber optic device for viewing the surgery. One or more additional trocar tubes are introduced through incisions in the abdominal wall such that laparoscopic surgical tools can be inserted through the tube(s) for manipulating, cutting and/or suturing an internal organ or tissue. In this manner, while viewing a video monitor via the fiber optic device positioned in the navel trocar, the surgeon can grasp an organ or tissue with one surgical tool and simultaneously cut or suture with another surgical device.

The evolution of minimally invasive surgery has given rise to the need of single-shaft surgical instruments which can be inserted through a trocar and easily manipulated by a surgeon. These instruments are fashioned such that they can be inserted lengthwise through the trocar and comprise hand-held controls on the proximal end thereof to operate the distal, tissue-manipulating end of said instrument. Single shaft devices must have a sufficiently small diameter so that they can be inserted into a trocar tube and guided to the operative tissue site. Typically, such instruments are designed to perform one function, such as grasping and stabilizing tissue, cutting tissue, holding a suturing needle or pulling a suturing needle through tissue, suctioning and irrigating the fluids, cauterizing the tissue, coagulating blood vessels and so on. A major drawback to minimally invasive surgery is that it requires exceptional motor coordination to grasp and stabilize an organ or tissue with one surgical tool and performing a cutting or suturing procedure on said organ or tissue with a second surgical device, all while viewing a two dimensional video monitor. This disadvantage is particularly acute in performing a laparoscopic suturing procedure.

Figure 1:
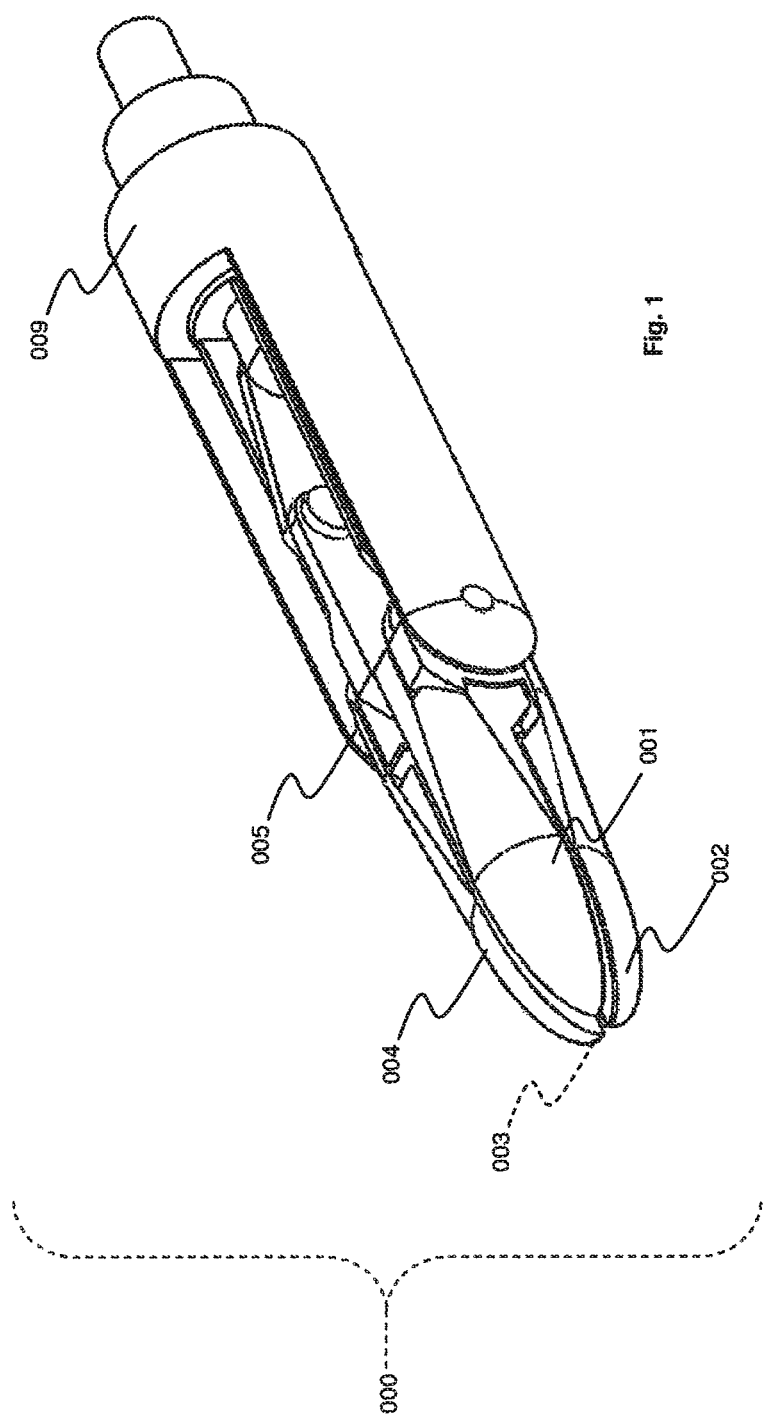
FIG. 1 is a perspective view of the preferred embodiment of the present invention showing the jaws in the closed position locked in the scissor configuration.
Figure 2:
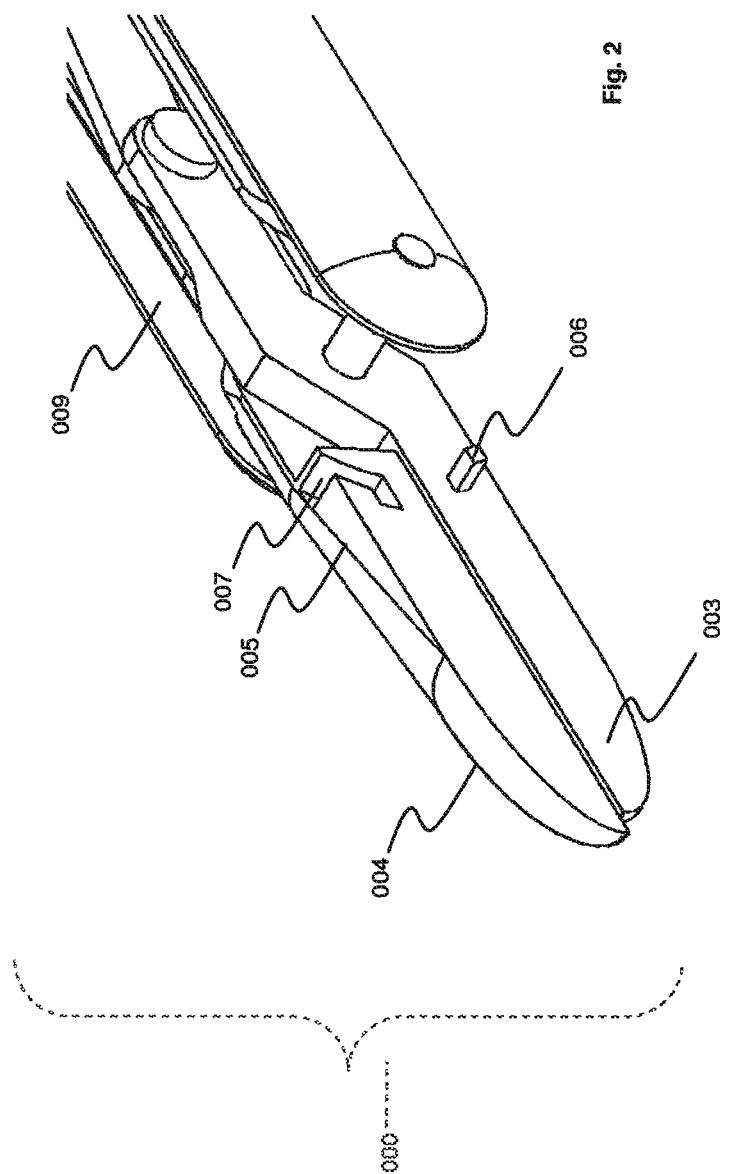
FIG. 2 is a perspective view of the preferred embodiment of the present invention showing the jaws in the closed position locked in the scissor configuration, but with two of the jaws not visible, so as to show the inner locking mechanism of the instrument.

FIG. 1 is a schematic side perspective view of the four jawed tip of the laparoscopic instrument proposed by the present invention. Also, FIG. 2 illustrates elements structurally integral to the jaws of the laparoscopic instrument proposed by the present invention which provide for interlocking action. Explanation as to construction of the laparoscopic tool subject of the present invention is now attempted referring to both these figures. The combinational scissor-grasper tool 000 comprises a bullet nosed end comprising four independent jaw elements 001, 002, 003 and 004. Said jaw elements are in operational association with a single hinge 005 and can lock into one another by positive locking mechanism enabled by mated protrusions and depressions corresponding to protrusion 006 and depression 007 along respective inner surface of each adjacent arm-in-pair. This mechanism ensures that when motion is delivered at the hinge, at all times, a specific combination of arms moves together.

Figure 3:
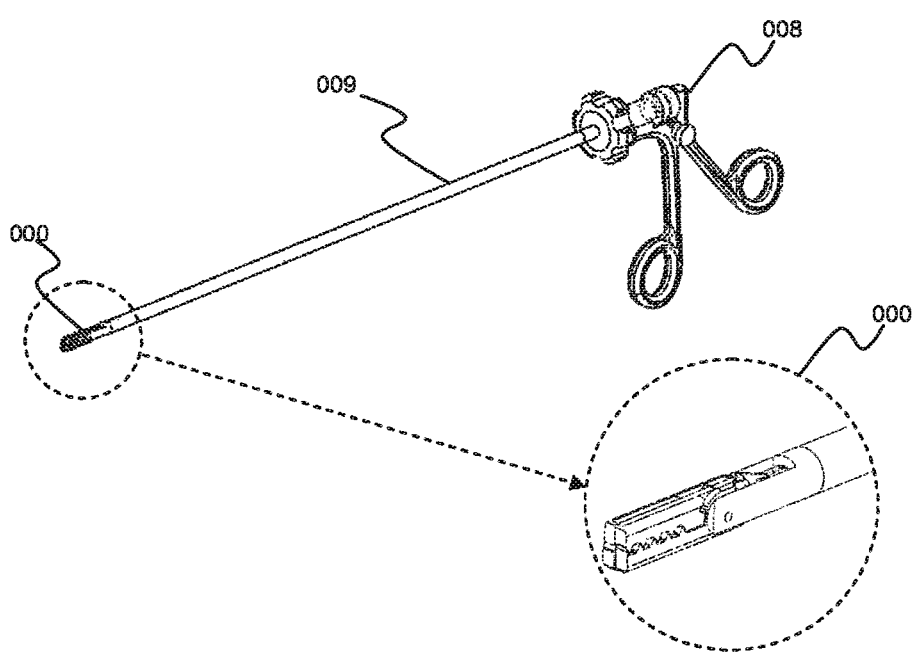
FIG. 3 is a perspective view of the laparoscopic instrument proposed by the present invention with a magnified view of the four-jawed tip shown in inset.
Figure 8:
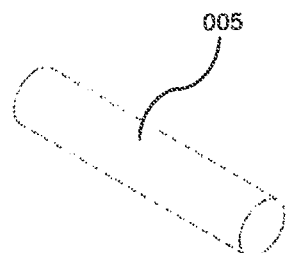
FIG. 8 illustrates the hinge, described as element 005 in FIGS. 4 and 5
Figure 9:
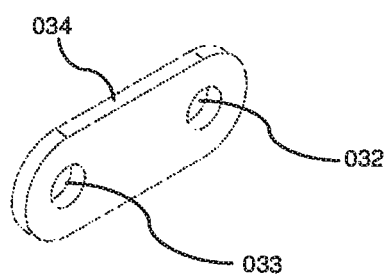
FIG. 9 illustrates the connecting link that enables force to get transmitted to jaw elements 001 and 003.
Figure 10:
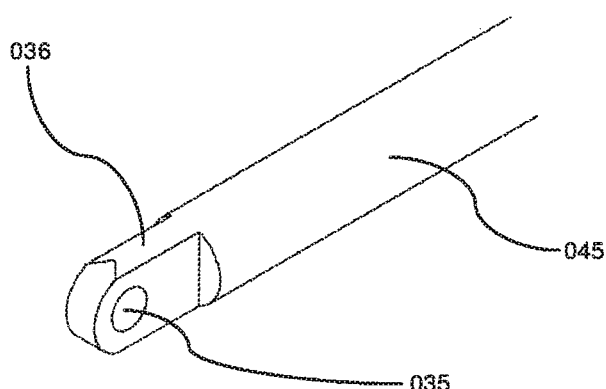
FIG. 10 illustrates the inner shaft that connects to the connecting link shown in FIG. 9.
Figure 11:
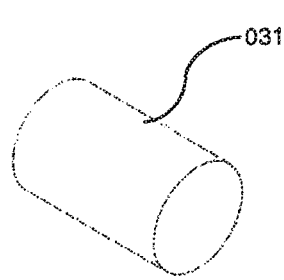
FIG. 11 illustrates the hinge member that resides within the distal end of the inner shaft.
Figure 12:
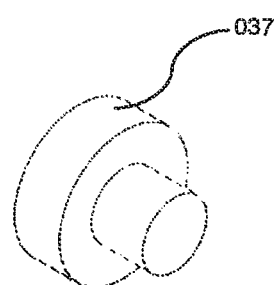
FIG. 12 illustrates the pin that allows the connecting link to hinge with jaws 001 and 003.
Figure 13:
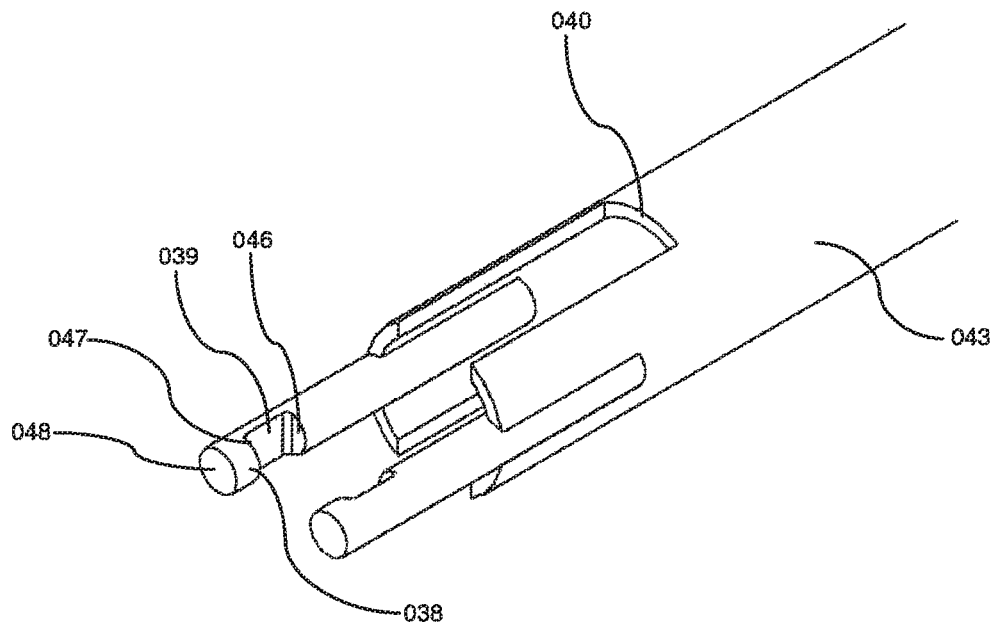
FIG. 13 illustrates the shifter shaft that engages the jaw elements 002 and 004 in order to push them forward or pull them backward in order to respectively convert the tool from the grasper mode to scissor mode or the other way round.
Figure 14:
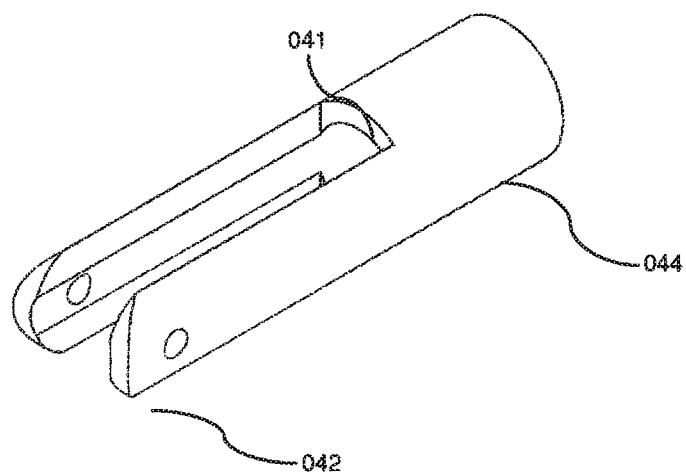
FIG. 14 illustrates the outer holder of the tool that holds all the jaws together on the hinge 005, and attaches to the outer shaft 009.

FIG. 3 illustrates magnified view of the four-jawed tip of the laparoscopic instrument proposed by the present invention. As illustrated therein, the four jawed tip 000 is key novel feature of the present invention capable of performance between both cutting and grasping functionalities via actuation of controller 008.

FIGS. 4 (a,b,c) and 5 (a,b,c) are schematic representation of inter-play between two jaw pairs when in grasping and cutting configurations respectively. When viewed from its tip with the tool being oriented such that its hinge 005 hosting the jaw elements 001, 002, 003 and 004 is parallel to the floor (horizontal), locking of jaw 001 with 004 and jaw 002 with 003 respectively to each other results in grasper configuration of the tool. In same orientation, locking of the left side jaws 003 and 004 and right side jaws 001 and 002 respectively to each other results in the scissor configuration of the tool 000.

Figure 16:
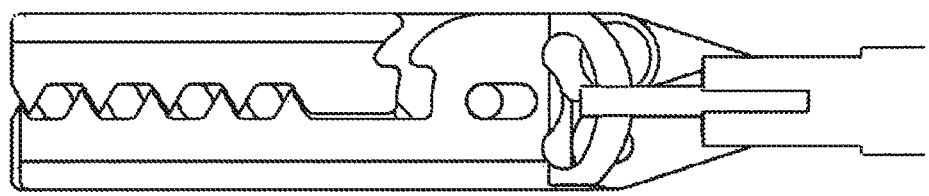
FIG. 16 illustrates the side view of the proposed instrument in the grasper configuration, with the jaws in closed position. Outer holder is hidden in this view.
Figure 17:
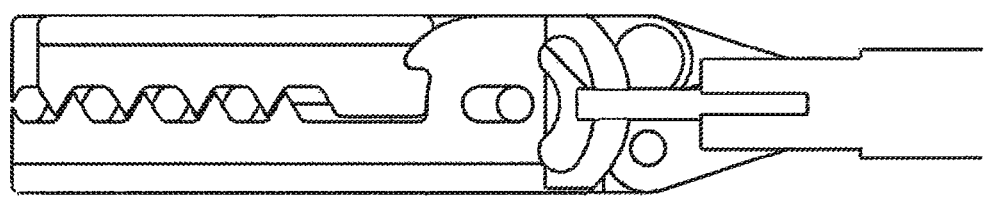
FIG. 17 illustrates the side view of the proposed instrument in the scissor configuration, with the jaws in closed position. Outer holder is hidden in this view.
Figure 19:
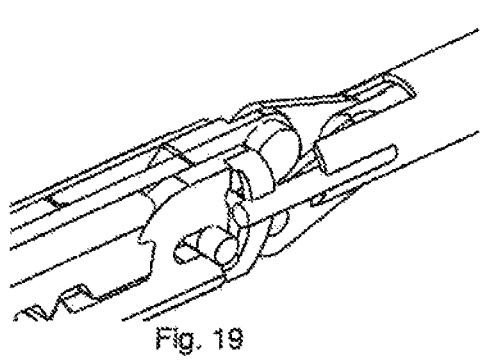
FIG. 19 illustrates a close-up perspective view of the inner mechanism of the instrument in the scissor configuration with the jaws in closed position. Outer holder is hidden in this view.
Figure 20:
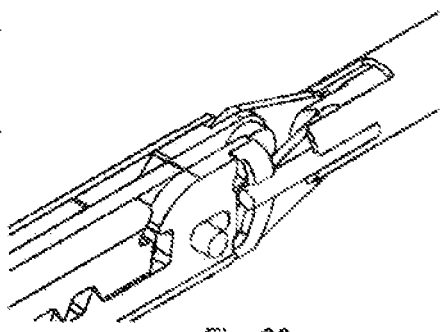
FIG. 20 illustrates a close-up perspective view of the inner mechanism of the instrument in the grasper configuration with the jaws in closed position. Outer holder is hidden in this view.

FIG. 6 (a,b,c) are front, perspective and back views of jaw element 002/004 of the laparoscopic instrument 000. It may be seen that 010 is a depression into which the extension 021 illustrated later in FIG. 7.a enters while the instrument is in the scissor configuration. Generally referring to FIGS. 6 to 17, it may be seen that the shape associated with the depression 010 is intended to mate with shape associated with extension 021 so that the two elements can snugly slide into one another. 011 is an arc section having its geometric centre at point 012 which is geometrically mimicked on the inner arc of extension 021 thus allowing the extension 021 to slide over arc section 011 smoothly. This motion is later described in FIG. 15. Points 012 and 013 determine the end-points of slot 027. The hinge 005 fits into the slot 027. Along the slot 027 jaws 004 and 002 can slide backward and forward such that either points 012 or 013 align with central axis of hinge 005, to enable the instrument to function as a grasper or as a scissor, respectively. Jaws 004 or 002 can rotate about hinge 005 either about point 012 or point 013. Arcs 014 and 015 define a slot 020. The arc 014 has its geometric centre at point 013, while the arc 015 has its geometric center at point 012. Protrusion 038 is positioned within the slot 020. Arcs 015 and 016 define the handle 028. The arc 016 has its geometric centre at point 013. This handle gets positioned into the depression 039. When the instrument shifts from grasper to scissor position, the shifter shaft 043 moves forward, towards the distal direction. During this forward motion, the proximal vertical surface 046 of the depression 039 pushes against the surface 016. At the same time, the distal surface 048 pushes against surface 014. This pushes the jaws 004 and 002 forward, towards the distal direction such that they slide on hinge 005 along their respective slots 027 taking them from being hinged about point 012 to being hinged about point 013. As a result of this motion, the protrusion 021 in jaws 001 and 003 gets inserted into depression 010 in jaws 002 and 004 respectively, thus locking jaw 001 to 002 and jaw 003 to 004. During the same motion, the protrusion 006 in jaws 001 and 003 slides out of the depression 007 in jaws 004 and 002 respectively, thus removing the lock between jaws 002 and 003 and between jaws 001 and 004. This is the scissor configuration. When the instrument shifts back from scissor to the grasper configuration, the shifter shaft 043 moves backwards, towards the proximal end. During this motion, the distal vertical surface 047 of depression 039 engages with the surface 015. This pulls the jaws 004 and 002 backwards, towards the proximal direction such that they slide on hinge 005 along their respective slots 027 taking them from being hinged about point 013 to being hinged about point 012. As a result of this motion, the protrusion 021 in jaws 001 and 003 gets removed from depression 010 in jaws 002 and 004 respectively, thus unlocking jaw 001 from 002 and jaw 003 from 004. During the same motion, the protrusion 006 in jaws 001 and 003 slides into the depression 007 in jaws 004 and 002 respectively, thus engaging the lock between jaws 002 and 003 and between jaws 001 and 004. This is the grasper configuration. Thus, the protrusion 021 and depression 010 form a male-female pair to lock the device in the scissor configuration. The protrusion 006 and depression 007 form another male-female pair to lock the device in the grasper configuration. This switching mechanism between grasper and scissor configurations is shown between FIG. 16 to FIG. 17 as a side view and also between FIG. 20 and FIG. 19 as a close-up perspective view.

When the instrument is in the scissor configuration, the jaws 004 and 002 rotate about the point 013 on hinge 005. In this configuration, the shifter shaft 043 has kept the jaws 004 and 002 pushed in this position. Hence, the surfaces 046 and 048 slide over surfaces 016 and 014 respectively. As the jaws 004 and 002 rotate about point 013, it is essential that the arcs 014 and 016 have their geometric centers at point 013. When the instrument is in the grasper configuration, the jaws 004 and 002 rotate about the point 012 on hinge 005. In this configuration, the shifter shaft 043 has kept the jaws 004 and 002 pulled in this position. Hence, the surface 047 slides over surface 015. As jaws 004 and 002 rotate about point 012, it is essential that the arc 015 has its geometric centre at point 012.

While shifting between scissor and grasper configurations, a single stroke motion engages one lock and disengages the other. The serrated surfaces 017 of jaws 004 or 002 and serrated surfaces 026 of jaws 001 and 003 are used for the grasping action. The distance between each tooth of the serrated surfaces 017 and 026 is greater than or equal to the distance between points 012 and 013. While the tool jaws are in the closed position and the tool needs to be shifted between scissor and grasper configurations in either direction, this particular distance between the teeth on serrated surfaces 017 and 026 ensures that jaw 004 can slide over jaw 003 and jaw 002 can slide over jaw 001, without letting the teeth physically interfere with each other.

According to another aspect of the present invention, edge 018 of jaws 004 or 002 is hardened and angled to create a sharp shearing edge. As shown in FIG. 5.b and FIG. 18, the edge 018 in jaw 004 moves against the edge 018 of jaw 002 to create the necessary shearing action required for the instrument to function as a scissor.

The serrated surfaces 017 and 026 are physically distinct and independent of the shearing edge 018. This makes it possible to pick a great variety of grasping serration independently of a variety of scissor edge. Thus, a large number of combinations of different scissor and grasper types are possible to be incorporated in the instrument.

According to another aspect of the present invention, the handle 028 is created with a step 019 such that the depression 039 can be accommodated with the protrusion 038 positioned in the slot 020.

The protrusion 021 is of a shape comprising an arc with the geometric centre at point 023. This curvature also matches with the curvature of depression 010. The depression 022 is of a shape comprising an arc with the geometric centre at point which is offset towards the distal end of the tool from point 023 by a distance that is equal to the distance between points 012 and 013. This is also the distance by which the shifter shaft 043 moves while switching between the scissor and grasper mechanisms. Point 023 is the position of a hole in jaws 001 or 003 in which the hinge 005 resides. Jaws 001 and 003 always rotate about the axis through point 023.

The connecting link 034 hinges to the jaws 001 and 003 at the hole 024 using pin 037. Pin 037 can be in the form of a rivet that joins holes 033 and 024. A step 025 accommodates the thickness of the connecting link 034. Inner shaft 045 has a means of connecting with link 034 by a pin 031 at holes 032 and 035. The pin 031 can be in the form of a rivet.

Figure 15:
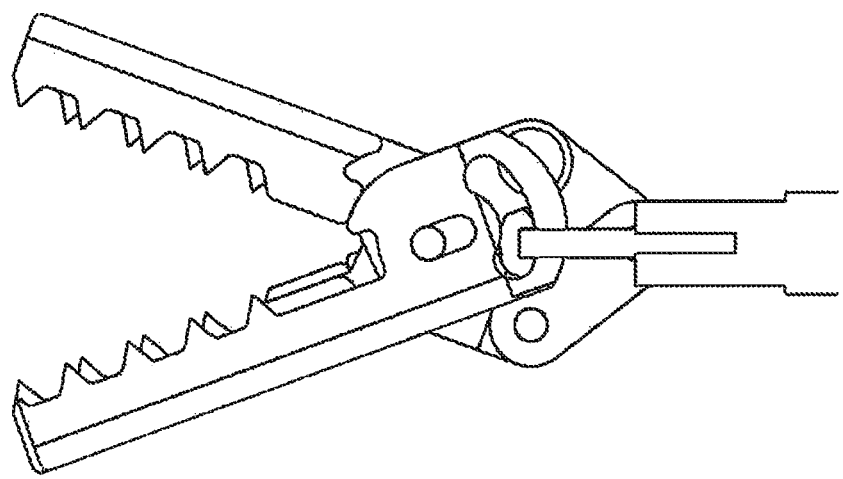
FIG. 15 illustrates the side view of the proposed instrument in the grasper configuration, with the jaws in open position. Outer holder is hidden in this view.
Figure 21:
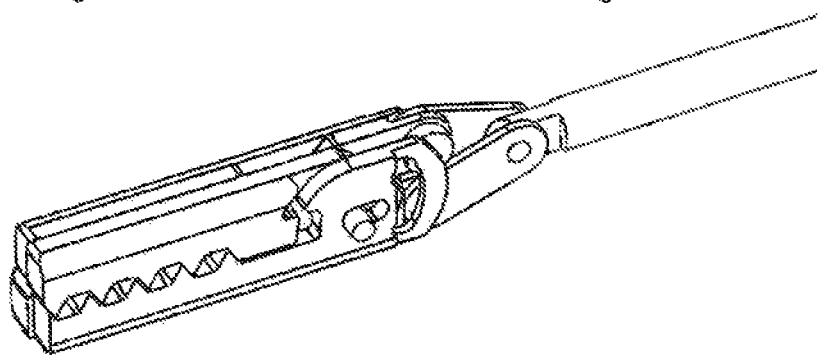
FIG. 21 illustrates a perspective view of the inner mechanism of the instrument in the grasper configuration, with the jaws in closed position and the connecting links visible. Outer holder and shifter shaft are hidden in this illustration.

The entire system of the inner shaft 045 connected to jaws 001 and 003 by means of connecting links 034 hinged respectively at 032 and 033 by pins 031 and 037, is shown in FIG. 21. The jaws 001 and 003 are forced to open by a simple parallelogram mechanism when the inner shaft 045 is moved forward in the distal direction. The connecting links 034 and the distance between points 023 to 024 on jaws 001 and 003 form the segments of this parallelogram mechanism. The user's action at element 008 creates this required motion in 045. When the proposed surgical tool is in the grasper configuration, the protrusion 006 in jaws 001 and 003 locks in with depression 007 in jaws 004 and 002 respectively, thus locking jaws 001 and 004 together on one hand, and jaws 002 and 003 on the other. At this time the protrusion 021 in jaws 001 and 003 and depression 010 in jaws 002 and 004 are no longer engaged. When the jaws 001 and 003 are forced to open up by the parallelogram mechanism movement initiated by the user acting on inner shaft 045, they also, in turn force jaws 004 and 002 to move along with them respectively. This creates the grasper configuration as shown in FIG. 15 and FIGS. 4.*a*, 4.*b*, 4.*c*.

Figure 18:
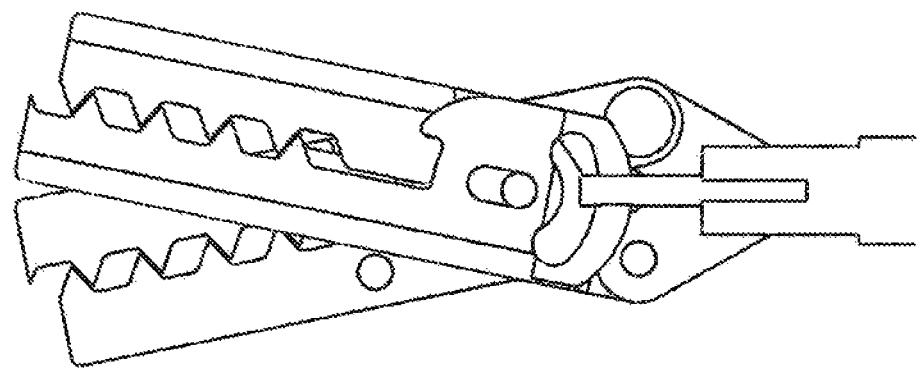
FIG. 18 illustrates the side view of the proposed instrument in the scissor configuration, with the jaws in open position. Outer holder is hidden in this view.

When the tool is in the scissor configuration, the protrusion 021 in jaws 001 and 003 locks in with depression 010 in jaws 002 and 004 respectively, thus locking jaws 001 and 002 together on one hand, and jaws 004 and 003 on the other. At this time the protrusion 006 in jaws 001 and 003 and depression 007 in jaws 004 and 002 respectively are no longer engaged. When the jaws 001 and 003 are forced to open up by the parallelogram mechanism movement initiated by the user acting on inner shaft 045, they also, in turn force jaws 002 and 004 to move along with them respectively. This creates the scissor configuration as shown in FIG. 18 and FIGS. 5.*a*, 5.*b*, 5.*c*.

Thus, when the instrument is in the grasper configuration, jaw 004 locks with jaw 001 while jaw 003 locks with jaw 002. On the other hand, when the instrument is in the scissor configuration, the jaw 004 locks with jaw 003 while jaw 001 locks with jaw 002.

A step 036 is created at the distal tip of inner shaft 045 in order to accommodate the thickness of connecting link 034. The combined widths of the section 036 and two instances of link 034 are accommodated by pin 031 within the cut out gap 040 of shifter shaft 043. This in turn must fit within the cut out gap 041 of outer holder 044. In this outer holder 044 the hole 042 holds the hinge 005.

A means to provide for the backward and forward movement of the shifter shaft is created. Any standard method to achieve this in a user-friendly manner would work. Other requirements of a surgical instrument, such as the ability rotate and fit within a 5 mm diameter, are also fulfilled.

According to another aspect of the present invention, the surfaces involved in grasping and cutting are independent of each other. Hence they may be sharpened, knurled, and formed independently for optimal performance.

Since both scissor and grasper operate about the same common hinge 005, there is no inherent need for a 90° rotation about the tool's axis for a shift of configuration.

As described hereinabove, the mechanism for interlocking of jaw elements comprises male and female locking elements. Said interlocking elements are completely internal to the jaws themselves and thus do not interfere with the surgical environment.

According to another aspect of the present invention, the mechanism to shift between the grasper and scissor configurations is also contained completely internal to arm of the tool. It has so been designed to allow the tool to be manufactured within a 5 mm diameter. It should be appreciated that the instrument can be provided with a different shape of jaws to perform other actions besides straightforward grasping and cutting. Different types of graspers, scissors can be incorporated to this mechanism. The actuation of the instrument may be carried out by either the means of a regular handle operated by hands or it can be motorized to be applied in a robotic setting. In either case the mechanism of the front tip does not change.

If the jaw members and internal mechanism members are coated with appropriate insulation layers, the function of bipolar cauterization may also be added into the tool. The bipolar cauterization will occur between the jaw elements when the instrument is in the grasper configuration.

According to yet another aspect of the present invention, the mechanism to shift between the grasper and scissor configurations operates with a strictly linear motion along the axis of the tool. Inner and outer shafts of the main shaft body 009 are separable and thus, allow for rotation along the longitudinal axis. This allows for the tool to be rotated infinitely clockwise or anticlockwise about the axis of its main shaft body 009 and thus enable a 360° field of operation.

According to another aspect of the present invention, it is intended by the present inventor to make the device of the present invention amendable to controllers of common art, thus negating design of customized control architecture and/or user interfaces. This also means easy migration between tools for surgeons.

Thus, it would be now evident to the reader that the user interface or controlling means is same for both cutting as well as grasping functions and that the selection of function is enabled via actuation of a switch which controls interlocking of pairs of jaws of the device proposed by the present invention in accordance with functionality required. This switch may be selected among common art easy switching mechanisms such as turning knobs, trigger or toggle levers. Thus, the user has ability to migrate from one mode of operation to other with single stroke of switch and without having to remove/reinsert in body of patient being operated. Further, the scissor grasper combination can be made able to withstand infinite rotation of the tool along its longitudinal axis using a common art thumb-wheel. As common art controllers are utilized, the user maintains same tactile feel and dexterity while adapting to use of the proposed tool.

According to other embodiments of the present invention, the inner shafts of the tool are constructed to allow disassembly and reassembly to the main outer shaft by means chosen among press-fit, threading/screw mechanism or keyslot mechanism. This makes it possible to easily autoclave or sterilize the tip of the proposed instrument. It also allows for just the tip to be replaced without having to replace the handle or outer shaft.

According to another embodiment of the present invention, a cleaning port may be introduced in the shaft of the proposed laparoscopic tool for allowing sterilization and multiple use thereafter.

As will be realized, the present invention is capable of various other embodiments and that its several components and related details are capable of various alterations, all without departing from the basic concept of the present invention. Accordingly, descriptions will be regarded as illustrative in nature and not as restrictive in any form whatsoever. Modifications and variations of the system and apparatus described herein will be obvious to those skilled in the art. Such modifications and variations are intended to come within the scope of the appended claims.

We claim:

1. An apparatus comprising:
   first, second, third, and fourth jaw elements, the first jaw element comprising a first extension and a first protrusion, the third jaw element comprising a second extension and a second protrusion, the second jaw element comprising first and second depressions, and the fourth jaw element comprising third and fourth depressions;
   wherein in a first configuration, the second jaw element is coupled to the first jaw element by the first extension received in the first depression, and the fourth jaw element is coupled to the third jaw element by the second extension received in the third depression; and
   wherein in a second configuration, the second jaw element is coupled to the third jaw element by the second protrusion received in the second depression, and the fourth jaw element is coupled to the first jaw element by the first protrusion received in the fourth depression.

2. The apparatus of claim 1, further comprising:
a shifter shaft comprising a proximal end and a distal end;
wherein the distal end of the shifter shaft is coupled to the second and fourth jaw elements;
wherein a longitudinal axis is defined through the proximal and distal ends of the shifter shaft;
wherein on the condition the shifter shaft is in a first position along the longitudinal axis, the apparatus is in the first configuration; and
wherein on the condition the shifter shaft is in a second position along the longitudinal axis, the apparatus is in the second configuration.

3. The apparatus of claim 2, wherein:
the first, second, third, and fourth jaw elements each comprise a serrated surface;
the serrated surfaces of the first and second jaw elements are configured to engage each other; and
the serrated surfaces of the third and fourth jaw elements are configured to engage each other.

4. The apparatus of claim 3, wherein:
each serrated surface comprises adjacent teeth on a surface separated by a distance equal to or larger than a distance between the first and second positions of the shifter shaft.

5. The apparatus of claim 2, further comprising:
a hinge;
wherein each of the first, second, third, and fourth jaw elements rotate about the hinge.

6. The apparatus of claim 5, wherein:
each of the second and fourth jaw elements comprise a first slot; and
the hinge moves along the first slots of the second and fourth jaw elements in a direction parallel to the longitudinal axis.

7. The apparatus of claim 5, wherein:
each of the second and fourth jaw elements comprise a second slot defined by two arcs; and
the distal end of the shifter shaft is configured to engage the second slots of the second and fourth jaw elements to shift the second and fourth jaw elements relative to the hinge on the condition the shifter shaft is moved between the first and second positions.

8. The apparatus of claim 7, further comprising:
an inner shaft comprising a distal end;
a pair of connecting links each coupled to the distal end of the inner shaft; and
a common pin;
wherein a first link of the pair of connecting links is coupled to the first jaw element;
wherein a second link of the pair of connecting links is coupled to the third jaw element;
wherein the first jaw element and the third jaw element each comprise a hole; and
wherein the common pin is inserted through the holes in the first and third jaw elements.

9. The apparatus of claim 2 embodied in a medical device, wherein:
the first configuration is a cutting configuration of the medical device; and
the second configuration is a grasping configuration of the medical device.

10. The apparatus of claim 1 embodied in a medical device, wherein:
the first configuration is a cutting configuration of the medical device; and
the second configuration is a grasping configuration of the medical device.

11. A method for configuring first, second, third, and fourth jaw elements into first and second configurations, the method comprising:
configuring the first, second, third, and fourth jaw elements into the first configuration by causing the second and fourth jaw elements to respectively couple to the first and third jaw elements by first and second depressions receiving first and second extensions, respectively; and
configuring the first, second, third, and fourth jaw elements into the second configuration by causing the second and fourth jaw elements to respectively couple to the third and first jaw elements by third and fourth depressions receiving first and second protrusions, respectively;
the first and second extensions being provided on the first and third jaw elements respectively, and the first and second protrusions being provided on the first and third jaw elements, respectively; and
the first and second depressions being provided on the second and fourth jaw elements, respectively, and the third and fourth depressions being provided on the second and fourth jaw elements, respectively.

12. The method of claim 11, further comprising:
in the first configuration, creating a cutting motion with the first, second, third, and fourth jaw elements by translating an inner shaft coupled at a distal end to the first and third jaw elements; and
in the second configuration, creating a grasping motion with the first, second, third, and fourth jaw elements by translating the inner shaft.

13. The method of claim 11, wherein:
the distal end of a shifter shaft is coupled to the second and fourth jaw elements;
the configuring of the first, second, third, and fourth jaw elements into the first configuration comprises placing the shifter shaft in a first position along a longitudinal axis; and
the configuring of the first, second, third, and fourth jaw elements into the second configuration comprises placing the shifter shaft in a second position along the longitudinal axis.

14. The method of claim 11, wherein the method comprises configuring a surgical instrument into the first and second configurations.

* * * * *